(12) United States Patent
Cho et al.

(10) Patent No.: US 6,180,108 B1
(45) Date of Patent: Jan. 30, 2001

(54) VECTORS HAVING TERMINAL REPEAT SEQUENCE OF EPSTEIN-BARR VIRUS

(75) Inventors: Myung-Sam Cho, Pinole; Sham-Yuen Chan, El Sobrante, both of CA (US)

(73) Assignee: Bayer Corporation, Pittsburgh, PA (US)

( * ) Notice: Under 35 U.S.C. 154(b), the term of this patent shall be extended for 0 days.

(21) Appl. No.: 09/209,915

(22) Filed: Dec. 10, 1998

(51) Int. Cl.[7] .......................... A61K 39/12; C12N 15/00; C12N 1/12

(52) U.S. Cl. ..................................... 424/199.1; 424/204.1; 435/320.1; 435/235.1; 435/239; 435/91.1; 435/91.33

(58) Field of Search ................................ 435/320.1, 91.1, 435/91.33, 235.1, 239; 424/199.1, 204.1

(56) References Cited

PUBLICATIONS

Sadler et al. Journal of Virology, Jul. 1995, vol. 69, No. 7, pp. 4577–4581.*

* cited by examiner

Primary Examiner—Ali R. Salimi

(57) ABSTRACT

The use of a unique terminal repeat sequence derived from Epstein-Barr virus to improve the integration frequency of heterologous expression vectors in transfected cells is described. The vectors can be used in a process for deriving high producing cell lines.

9 Claims, 3 Drawing Sheets

| | | | | |
|---|---|---|---|---|
| GGCAATGGAG | CGTGAAGAAG | GGCCCCAGGG | CTGACCCCGG | CAAACGTGAC | (50)
| CCGGGGCTCC | GGGGTGACCC | AGGCAAGCGT | GGCCAAGGGG | CCCGTGGGTG | (100)
| ACACAGGCAA | CCCTGACAAA | GGCCCCCCAG | GAAAGACCCC | CGGGGGGCAT | (150)
| CGGGGGG*GTG* | *TTGGCG*__GGTC__ | __ATGGGG__GGGG | CGGGTCATGC | CGCGCATTCC | (200)
| TGGAAAAAGT | GGAGGGGGCG | TGGCCTTCCC | CCCGCGGCCC | CCTAGCCCCC | (250)
| CCGCAGAGAG | CGGCGCAACG | GCGGGCGAGC | GGCGGGGGGT | CGGGGTCCGC | (300)
| GGGCTCCGGG | GGCTGCGGGC | GGTGGATGGC | GGCTGGCGTT | CCGGGGATCG | (350)
| GGGGGGGGTC | GGGGGGCGCT | GCGCGGGCGC | AGCCATGCGT | GACCGTGATG | (400)
| AG | | | | | (402)

Fig._1

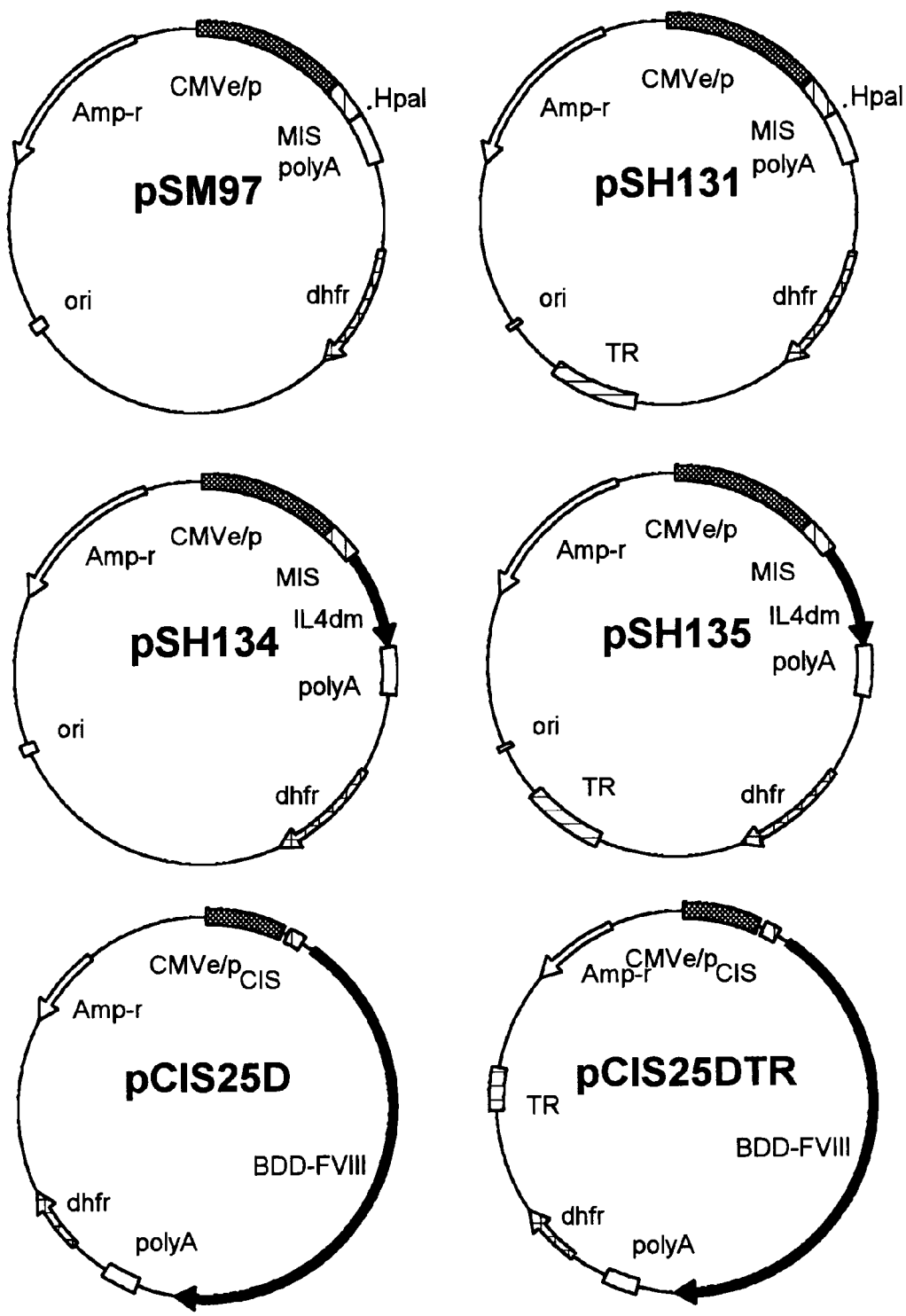
Fig._2

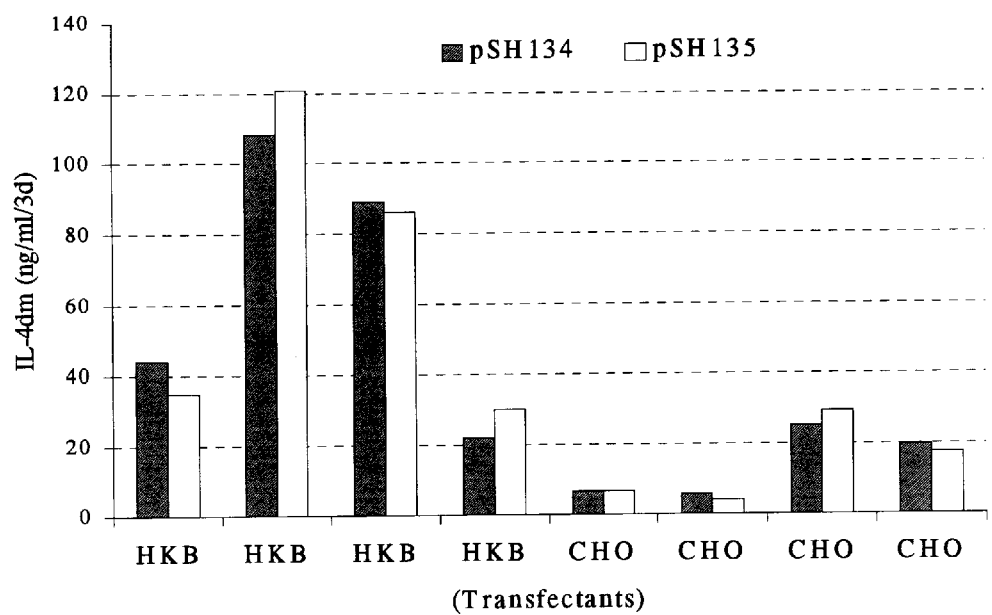
Fig._3

SEQUENCE LISTING

```
<160> NUMBER OF SEQ ID NOS: 1

<210> SEQ ID NO 1
<211> LENGTH: 402
<212> TYPE: DNA
<213> ORGANISM: Artificial Sequence
<220> FEATURE:
<223> OTHER INFORMATION: Description of Artificial Sequence:Derived from
      Epstein-Barr virus

<400> SEQUENCE: 1
ggcaatggag cgtgacgaag ggccccaggg ctgacccgg caaacgtgac ccggggctcc      60
ggggtgaccc aggcaagcgt ggccaagggg cccgtgggtg acacaggcaa ccctgacaaa    120 ggcccccag gaaagacccc cggggggcat cgggggggtg ttggcgggtc atgggggggg    180
cgggtcatgc cgcgcattcc tggaaaaagt ggaggggcg tggccttccc cccgcggccc     240
cctagccccc ccgcagagag cggcgcaacg gcgggcgagc ggcgggggt cggggtccgc    300 gggctccggg ggctgcgggc ggtggatggc ggctggcgtt ccggggatcg ggggggggtc    360 gggggcgct gcgcgggcgc agccatgcgt gaccgtgatg ag                        402
```

VECTORS HAVING TERMINAL REPEAT SEQUENCE OF EPSTEIN-BARR VIRUS

RELATED APPLICATIONS

The application to Cho designated MSB-7241, "Human hybrid host cell for mammalian gene expression," and the application to Cho et al. designated MSB-7255, "Expression system for factor VIII," contain related subject matter. Both applications were filed on the same day as the current application and are incorporated herein by reference.

BACKGROUND OF THE INVENTION

1. Field

This invention relates generally to the production of biologically active proteins from genetically engineered mammalian cell lines. Specifically, the invention is concerned with a novel expression vector containing an Epstein-Barr virus terminal repeat sequence which enhances integration of expression vectors into the genomic DNA in host mammalian cell lines.

2. Background

Many attempts have been made to increase the stable integration efficiency of expression vectors into genomic DNA by site specific integration.

Random, nonhomologous integration of input DNA into the host cell genome occurs more than 100 times more frequently than targeted homologous recombination (Thomas et al., 1987, Cell 51: 503–512). However, homologous recombination using hotspot, e.g. hypervariable minisatellite DNA, was shown to occur more frequently than random recombination between two defective plasmids in mammalian cells (Wahls et al., 1990, Cell 60: 95–103).

Autoantigenic cellular protein was isolated by Sun et al. (1994, Proc Natl Acad Sci USA 91: 8646–8650). This protein was identified as terminal repeat binding protein, or TRBP. Two terminal repeat binding sites (TRBS1 and TRBS2) for terminal repeat binding protein were also identified by Sun et al. They observed that TRBP binds sequences present in repetitive cellular DNA, e.g. variable-number tandem repeats (VNTR) and immunoglobulin heavy chain class switch regions.

The terminal repeat binding protein binds to G-rich regions of terminal repeats of Epstein-Barr virus (EBV-TR). EBV-TR takes part in processing and packaging of virion DNA (Zimmermann et al., 1995, J Virol 69: 3147–3155). The EBV-TRs are involved in the integration into chromosomal DNA (Matsuo et al., 1984, Science 226: 1322–1325) and in the circularization event of the genome after infection. These sequences are the essential elements for cleavage and packaging of the EBV virion DNA (Hammerschmidt et al., 1989, Nature (London) 340: 393–397; Zimmermann et al. J Virol, 1995, 69: 3147–3155). These data indicate the important role of the EBV-TR sequence in the recombination events. Therefore, we tested EBV-TR for integration events in deriving clones from the transfected cells.

SUMMARY OF THE INVENTION

We have now discovered that cells transfected with an expression vector containing a selectable marker and an EBV-TR sequence show a five to ten fold increase in the number of cells resistant to the selection agent as compared to cells transfected with the same expression vector without an EBV-TR sequence under the same selection conditions. The higher survival ratios under drug selection indicate that the vectors with EBV-TR may enhance the integration frequency of vectors into genomic DNA.

The expression vectors of this invention include an EBV-TR sequence and a selectable marker, such as dihydrofolate reductase (dhfr). The preferred EBV-TR sequence is a 402 bp sequence (given in FIG. 1) which includes the core part of the TRBP-binding region from an immortalized lymphoblastoid cell line 6F 11. In a preferred embodiment, the mammalian gene expression vector comprises a CMV enhancer and promoter, an intronic sequence (MIS, as described in U.S. Pat. No. 5,854,021 to Cho et al.) derived from Epstein-Barr virus, a unique restriction enzyme site HpaI to allow for insertion of a protein coding sequence, and a poly A region plus the plasmid backbone with a drug selection marker and the EBV-TR sequence indicated in FIG. 1. This vector is denoted pSH131 (see FIG. 2). This vector is used to introduce the appropriate DNA coding sequence of the protein of interest into mammalian cells to stabilize the protein expression in a long term culture in a serum-free medium. In one preferred embodiment, the sequence for an IL-4 mutein was cloned into pSH131 and the resulting vector is pSH135. The EBV-TR sequence was also directly linked to pCIS25D (vector for expressing B-domain deleted rFVIII, designated BDD-FVIII) and resulting vector is pCIS25DTR.

A preferred amplifiable marker is dihydrofolate reductase (dhfr) although other markers such as glutamine synthetase (gs) and multidrug-resistance gene (mdr) can be substituted. These amplifiable markers (dhfr, gs, and mdr) are also selectable markers. A preferred selectable marker is neo (aminoglycoside phosphotransferase, for neomycin resistance); still other preferred markers such as hph (hygromycin B phosphotransferase) and hisD (histidinol dehydroganase) can be substituted.

The cell host to be transfected can be any mammalian cells. Cell lines that are known to accept the integration of selection genes into their chromosomal DNA are optimal; for example, human embryonic kidney cells (e.g. 293S cells), human hybrid of 293S and B-cell origin (e.g. HKB11; ATCC deposit no. CRL 12568, see U.S. Patent application to Cho designated MSB-7241, "Human hybrid host cell for mammalian gene expression," filed on the same day as the current application and incorporated herein by reference), chinese hamster ovary (CHO), baby hamster kidney (BHK-21), mouse myeloma, and human B-cells.

As one working example, we show that CHO (dhfr-) cells transfected with an expression vector containing dhfr and an EBV-TR sequence showed about a five to ten fold increase in the number of methotrexate (MTX) resistant cells as compared to cells transfected with the same expression vector without EBV-TR under the same selection conditions.

As used herein, serum-free conditions means conditions in which cell growth occurs in media lacking any added serum.

BRIEF DESCRIPTION OF THE FIGURES

FIG. 1 shows the nucleotide sequence of the EBV-TR sequence used in the expression vector in the examples. (SEQ ID NO: 1) A 9 bp element (GTGTTGGCG) was written in italic and a shortened 11 bp element (GGTCATGGGG; 10 bp) was written in bold. A repeat of 11 bp (GGCGGGTCATG) was underlined.

FIG. 2 shows the expression vectors used to compare selection ratios. All plasmids are constructed based on a pBR322 backbone and contain a dhfr expression unit. All genes coding proteins of interest are under the regulation of CMVenhancer/promoter (CMVe/p), 5'-intron (MIS or CIS) was positioned at the 5'-end of the genes.

FIG. 3 shows the effect of the EBV-TR sequence on the expression of an IL-4 mutein from pSH134 and pSH135 in transient transfection assays repeated four times using CHO and HKB cells.

SPECIFIC EMBODIMENTS
Construction of expression vectors containing EBV-TR

A 381 bp fragment of the EBV-TR sequence described in FIG. 1, encompassing DNA sequence from 170,476 to 170,856 of B95/8 EBV sequencing data (P. J. Farrell, "Epstein-Barr Virus Genome," in Advanced Viral Oncology; edited by G. Klein; Ravens Press, Ltd.: New York 1989, pp 103–132) was made by polymerase chain reaction (PCR) from a template DNA prepared from 6F11 cells (ATCC CRL9562) a lymphoblastoid cell line which was immortalized by EBV. Two primers (5'-GGCAATGGAGCGTGACGAAG-3' and 5'-CTCATCACGGTCACGCATGG-3', fragments derived from SEQ ID:1) were made to amplify the 381 bp fragment of the EBV-TR sequence in 6F11 cell DNA. The PCR products were phosphorylated and linked to the expression vector pSM97 after removing a 553 bp fragment excised by the restriction endonuclease NaeI. The resulting vector was pSH131 (FIG. 2), which has been deposited with the American Type Culture Collection, ATCC 98879.

DNA sequencing data of the EVB-TR sequence in pSH131 (402 bp) was larger than the expected size (381 bp). The main difference is a repeat of 11-bp (GGCGGGTCATG) consisting of 4 bp from a 9 bp element (GTGTTGGCG)and 7 bp from a 10 bp element (GGTCATGGGG). Both ends of EBV DNA molecule in EBV-TR described by Zimmermann et al. (1996, J Virol 69: 3147–3155) consists of a 9 bp element (GTGTTGGCG) and a 11 bp element (GGGTCATGGGG) (all fragments derived from SEQ ID NO: 1). The 11 bp element in pSH131 lacked 1 bp; thus we observed only 10 bp. The reason for the observed repeat of the 11 bp element might be that the EBV-TR sequence in pSH131 (402 bp) was made using 6F11 DNA, not B95/8 DNA. 6F 11 cells are immortalized by an EBV and have a concatenated form of EBV-DNA (Cho and Tran, 1993, Virology 194: 838–842), while B95/8 EBV is an infecting virus. Therefore, the EBV-TR sequence in pSH131 (402 bp) was derived from this concatenated EVB-DNA.

A sequence of DNA coding for an IL-4 double mutein (IL-4dm) was inserted into the HpaI site of pSM97 and pSH131. The resulting plasmids are pSH134 (IL-4dm in pSM97) and pSH135 (IL-4dm in pSH13 1). The IL-4dm that was used is as essentially described in Eur. Pat. 0613499B1 to Sebald, incorporated herein by reference. This IL-4dm is a derivative of the unmodified IL-4 having the amino acids at position 121 (arginine) and 124 (tyrosine) changed to aspartic acid.

The PCR product of the EBV-TR sequence was also inserted into the SalI site of pCIS25D, which is an expression vector coding for B-domain deleted factor VIII (BDD-FVIII). The resulting plasmid is pCIS25DTR. All four expression vectors, pSH134 and pSH135, pCIS25D, and pCIS25DTR, have the same functional dhfr gene. See FIG. 2 for the maps.

EXAMPLE 1
Effect of EBV-TR on the expression of a reporter gene in transient transfection assays Two million CHO (dhfr-negative) and HKB (a human-human hybrid cell line; ATCC CRL-12568) cells were separately transfected with 5 ug of plasmid DNA (pSH134 and pSH135) in a 6-well plate using cationic liposome DMRIE-C reagent (Life Technologies, Rockville, Md.) according to the protocol provided. Two or three days after transfection of CHO and HKB cells with both expression vectors, the supernatants were tested for expression of the IL-4dm by an ELISA. As shown in FIG. 3, expression levels of IL-4dm from pSH134 were very similar with those from pSH135 from two different transfectants in repeated transient transfection assays. These results show that EBV-TR has no effects on the expression of the IL-4dm reporter gene. These results indicate that EBV-TR might not have any enhancing function on the gene expression in the vectors, e.g. dhfr. This implies that the presence of the EBV-TR increases survival ratios through a mechanism other than the increased expression level of dhfr gene, i.e. the mechanism may involve increased integration of the vector.

EXAMPLE 2
Drug selection of transfected cells with a vector containing EBV-TR CHO (dhfr-) cells were separately transfected with 5 $\mu$g of pSH134 and 5 $\mu$g of pSH135 using cationic liposome DMRIE-C reagent according the protocol provide by Life Technology. Transfected cells ($5\times10^5$ cells per 96 well plate) were selected in serum-free medium supplemented with r-insulin, transferrin and 50 nM MTX lacking hyphoxanthine and thymidine. Growth-positive wells were counted at 2-weeks after intitial selection in selection medium with 50 nM MTX. No MTX-resistant clones were derived from mock transfected cells. Results are shown in Table 1. Exp. 1 (IL-4dm) was performed in the serum-free medium lacking hypoxanthine and thymidine supplemented with 50 nM methotrexate. Exp.2 (IL-4dm) was performed in serum (5%) containing selection medium supplemented with 50 nM methotrexate. Exp.3 (BDD-FVIII) and Exp. 4 (BDD-FVIII) were performed in the serum-free selection medium as in Exp. 1.

TABLE 1

Drug-selection ratios from the transfected CHO (dhfr-) cells using the IL-4 dm and BDD-FVIII expression vectors linked with and without EBV-TR.

| | Growth-positive wells/total wells | | % growth of (2) over |
|---|---|---|---|
| | (1) Vector w/o EBV-TR[1] (growth+/total) | (2) Vector with EBV-TR[2] (growth+/total) | % growth of (1)[3] |
| Exp. 1 (IL-4 dm) | 28/960 (2.9%) | 238/960 (24.8%)[4] | 8.5 |
| Exp. 2 (IL-4 dm) | 51/576 (8.8%) | 520/864 (60.1%)[4] | 6.8 |
| Exp. 3 (BDD-FVIII) | 48/1344 (3.6%) | 2227/3840 (58%)[4] | 16 |
| Exp. 4 (BDD-FVIII) | 64/864 (7.4%) | 288/1056 (27%)[4] | 3.6 |

[1]Expression vectors lacking EBV-TR were used for transfection.
[2]Expression vectors containing EBV-TR were used for transfection.
[3]This ratio indicates growth+ ratios of cells transfected with the vector having EBV-TR over cells transfected with the vector lacking EBV-TR.
[4]Actual number of growth-positive colonies are much higher than growth-positive numbers counted from each well, because multiple colonies were growing in many growth-positive wells.

Two weeks after seeding the cells in selection medium, pSH135 (with EBV-TR) transfected cells showed an approximately 10 fold higher selection ratio than those transfected with pSH134 (without EBV-TR), although EBV-TR showed no enhancing function on IL-4 expression (FIG. 3). CHO (dhfr-) cells were also transfected with 5 µg of pCIS25D and 5 µg of pCIS25DTR using DMRIE-C reagent. Cells were selected under the same conditions as described above. Cells transfected with pCIS25DTR showed about 3-fold to about 16-fold higher selection ratio than those transfected with pCIS25D (Table 1). These results indicate that this sequence of EBV-TR in the expression vector can be used for increased integration of the vector in vivo for gene therapy.

EXAMPLE 3
Selection for high producing cell lines under serum-free conditions

CHO (dhfr-negative) cells transfected with pSH135 were plated onto 96-well plates (5×10$^5$ cells per plate) using a serum-free selection medium supplemented with transferrin, recombinant insulin, and methotrexate (50 nM). The selection medium lacks hypoxanthine and thymidine. After three months of amplification (50 and 100 nM MTX), one of the intitial populations, denoted 1G9, was adapted to suspension culture using a shake flask. The high level of IL-4dm productivity (~5 pg/c/d) was observed to continue for at least about 10 weeks in a serum-free and albumin-free medium supplemented with transferrin and recombinant insulin.

EXAMPLE 4
Stable integration

One of the CHO clones secreting BDD-FVIII, which was derived from pCIS25DTR transfected CHO cells as described in Example 2, was tested for its production stability under the absence of the selection drug (MTX). This clone continued to secrete BDD-FVIII during a six month period of growth in a medium lacking MTX. All single cell clones derived from this clone were also secretion positive. These results indicate that the integration of the vectors containing an EBV-TR sequence is a stable integration.

Conclusion

The derivation of stable cell lines which secrete high levels of proteins is a very tedious and labor-intensive task. This is at least partially due to the low chance of stable integration and amplification of the gene of interest. Large numbers of drug resistant clones generally need to be screened to obtain high secreting clones. Therefore, we have described here that vectors having an EBV-TR sequence result in an enhanced drug selection ratio, indicating a high integration ratio of transferred genes. As shown in Table 1, it was possible to select and to amplify transfected cells even under serum-free conditions.

The above examples are intended to illustrate the invention and it is thought variations will occur to those skilled in the art. Accordingly, it is intended that the scope of the invention should be limited only by the claims below.

What is claimed is:
1. An expression vector comprising a first DNA sequence coding for a heterologous protein, a second DNA sequence encoding an amplifiable marker, and an EBV-TR sequence.
2. An expression vector according to claim 1, wherein the amplifiable marker is dihydrofolate reductase.
3. A method of introducing an expression vector into mammalian cells in vitro comprising the steps of:
   a) contacting the mammalian cells with the expression vector under conditions which allow uptake of the expression vector by the cells, the expression vector comprising a first DNA sequence coding for a heterologous protein, a second DNA sequence encoding an amplifiable marker, and an EBV-TR sequence (SEQ ID NO:1);
   b) growing cells obtained from step a) in a selection medium under conditions which allow selection for resistant cells; and c) recovering cells obtained from step b) which express the heterologous protein.

4. The method of claim 3 further comprising the step of:
d) growing cells recovered in step c) under conditions which allow further selection to occur.

5. The method of claim 3 wherein the second DNA sequence encodes an amplifiable marker selected from the group consisting of dihydrofolate reductase, glutamine synthetase, and multidrug resistance gene.

6. The method of claim 3 wherein the first DNA sequence codes for a heterologous protein selected from the group consisting of factor VIII, derivatives of factor VIII, interleukin-4, and derivatives of IL-4.

7. The method of claim 4 wherein at least one of steps b) and d) occur under serum-free conditions.

8. A CHO clone designated 1G9 (ATCC Designation No. PTA-86).

9. A process for obtaining a CHO cell line which expresses IL-4dm, the process comprising the steps of
a) obtaining CHO cells,
b) contacting said CHO cells with a vector comprising an EBV-TR sequence (SEQ ID NO:1) and a coding sequence for IL-4dm under conditions which allow for the uptake of the vector by the cells,
c) establishing a CHO cell line which expresses IL-4dm from the result of step b).

* * * * *